United States Patent [19]

Lafon

[11] Patent Number: 4,576,944

[45] Date of Patent: Mar. 18, 1986

[54] 4-ETHYL-2-HYDROXY-3-METHYL-2-PHENYLMORPHOLINE, COMPOSITIONS AND USE

[75] Inventor: Louis Lafon, Paris, France

[73] Assignee: Laboratoire L. Lafon, France

[21] Appl. No.: 660,218

[22] Filed: Oct. 12, 1984

[30] Foreign Application Priority Data

Oct. 17, 1983 [FR] France .................. 83 16485

[51] Int. Cl.[4] .................. A61K 31/535; C07D 265/32
[52] U.S. Cl. ................................ 514/238; 544/173
[58] Field of Search ................... 544/173; 514/238

[56] References Cited

FOREIGN PATENT DOCUMENTS 791416 3/1958 United Kingdom .

Primary Examiner—Robert W. Ramsuer

Attorney, Agent, or Firm—Wegner & Bretschneider

[57] ABSTRACT

The present invention relates, by way of industrial products, to the 4-alkyl-2-hydroxy-3-methyl-2-phenyl-morpholine derivatives of the general formula

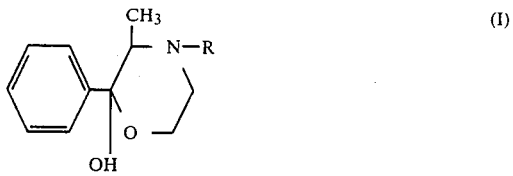

(in which R is a $C_1$–$C_4$ alkyl group) and their addition salts.

These products are useful in therapy, especially as stimulants and antidepressants for the CNS.

4 Claims, No Drawings

4-ETHYL-2-HYDROXY-3-METHYL-2-PHENYL-MORPHOLINE, COMPOSITIONS AND USE

The present invention relates to 4-alkyl-2-hydroxy-3-methyl-2-phenylmorpholine derivatives as new industrial products. It also relates to the method of preparation and the use in therapy (especially as stimulants and antidepressants for the CNS) of these new compounds.

It is known that a number of 2-phenylmorpholine derivatives have already been described in which the morpholinyl ring is substituted simultaneously in the 2-position and in the 4-position. Among these derivatives, compounds belonging to the family of the 4-alkyl-2-phenylmorpholines are known in particular from British Pat. No. 851,311, U.S. Pat. No. 2,997,469, the article by N. BUSCH et al., *Eur. J. Med. Chem. Chimica Therapeutica* 11 (No. 3), pages 201–207 (1976), French Pat. Nos. 7,443M and 71/38,592 (publication no. 2,111,882), French patent application No. 79/30,768 (publication no. 2,471,378) and European patent application No. 82/402,147.1 (publication no. 80,940). It is also known that several indications have been envisaged or recommended for 2,4-disubstituted compounds of the 4-alkyl-2-phenylmorpholine type. These compounds are presented, especially in the abovementioned publications, as excitants or stimulants for the CNS, tranquillizers, sedatives, anti-inflammatory agents, analgesics and antihypertensive agents.

2,2,4-Trisubstituted compounds are also known from French Pat. No. 1,535,615, namely 2,2-dimethyl-4-isopropylmorpholine, 2,2-dimethyl-4-(3-methylbutyl)-morpholine, 2,2-dimethyl-4-(2-phenylethyl)morpholine and 2,2-dimethyl-4-(2-phenylpropyl)morpholine.

Finally, U.S. Pat. No. 3,117,967 has disclosed 2-biphenyl-2-hydroxymorpholinium halides, presented as antiviral substances capable of being substituted in the 3-, 4- and 6-positions of the morpholinyl skeleton, and the article by D. R. MEYER, *Journal of Heterocyclic Chemistry* 18 (No. 3), pages 451–453 (1981), has disclosed 2,2,3,4-tetrasubstituted compounds of the 3-alkyl-2-hydroxy-2-phenyl-4-(2-hydroxyethyl)morpholine type, synthesized for their assumed anorexigenic properties.

It has just been found, surprisingly, that the 2,2,3,4-tetrasubstituted compounds according to the invention (and in particular 4-ethyl-2-hydroxy-3-methyl-2-phenylmorpholine and its addition salts), which are structurally different from the compounds known in the prior art, are even more valuable than the latter in therapy, especially as stimulants and antidepressants for the CNS.

The new compounds according to the invention, which belong to the family of the 2-phenylmorpholines, are selected from the group consisting of (i) the 4-alkyl-2-hydroxy-3-methyl-2-phenylmorpholine derivatives corresponding to the general formula

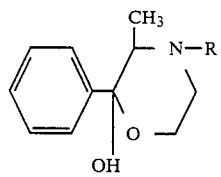

(I)

in which R is a $C_1$–$C_4$ alkyl group selected especially from $CH_3$, $CH_3CH_2$, $CH(CH_3)_2$ and $C(CH_3)_3$; and (ii) their addition salts.

The expression "addition salts" is understood here as meaning firstly the acid addition salts obtained by reacting a free base of the formula I with inorganic or organic acids, and secondly the ammonium salts. Hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular among the acids which can be used to salify the bases of the formula I. $CH_3I$ and $CH_3Cl$ may be mentioned in particular among the compounds making it possible to obtain ammonium salts. In general terms, the acid addition salts are preferred to the ammonium salts.

A number of compounds according to the invention are collated in Table I below without in any way implying a limitation.

TABLE I

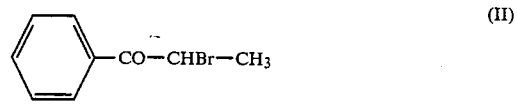

| Product | Code No. | R |
| --- | --- | --- |
| Example 1 (a) | CRL 41 000 | $CH_2CH_3$ |
| Example 2 (b) | CRL 41 000 A | $CH(CH_3)_2$ |
| Example 3 (a) | CRL 41 000 B | $CH_3$ |
| Example 4 (c) | CRL 41 000 C | $C(CH_3)_3$ |

Notes
(a): hydrochloride
(b): fumarate
(c): methanesulfonate

The compounds according to the invention which are preferred from the point of view of their therapeutic properties are 4-ethyl-2-hydroxy-3-methyl-2-phenylmorpholine and its acid addition salts, especially the hydrochloride.

The compounds of the formula I can be prepared in accordance with a method known per se, by the application of classical reaction mechanisms. The method recommended here consists in reacting α-bromopropiophenone of the formula

(II)

with an excess, relative to the stoichiometric conditions, of the 2-(N-alkyl)aminoethanol of the formula $$R-NH-CH_2-CH_2-OH \qquad (III)$$

in which R is defined as indicated above, in an inert solvent, especially dimethyl or diethyl ether.

About 2 mol of III will advantageously be used per mol of II, the reaction time being between 4 and 24 hours and the temperature being between 5° and 25° C.

According to the invention, a therapeutic composition is recommended which contains, in association with a physiologically acceptable excipient, at least one compound of the formula I or one of its addition salts as the active principle.

Of course, in a composition of this type, the active principle, which is selected from the group consisting of the compounds of the formula I and their nontoxic salts, is present in a pharmaceutically effective quantity.

Further advantages and characteristics of the invention will be understood more clearly on reading the following description of a preparative example and the results of pharmacological tests; these data as a whole do not imply a limitation but are given by way of illustration.

PREPARATION

Preparation of 4-ethyl-2-hydroxy-3-methyl-2-phenylmorpholine hydrochloride

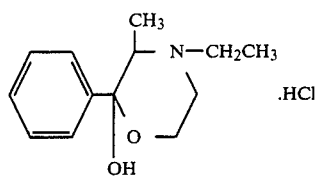

(Example 1; code no.: CRL 41 000)

50 g (0.235 mol) of α-bromopropiophenone are run dropwise into a solution of 41.78 g (0.469 mol) of 2-ethylaminoethanol in 800 ml of anhydrous ether. The reactants are left in contact for 24 hours, 500 ml of water are run in and the ether phase is decanted and washed with water. The ether phase is extracted with a mixture of 500 ml of water and 25 ml of concentrated HCl (d=1.19) and the aqueous phase is washed with ether. The aqueous phase is rendered alkaline to pH 11 by means of NaOH and extracted with ether, and the ether phase is washed with water and dried over $MgSO_4$. It is filtered, the hydrochloride is precipitated by means of a solution of hydrogen chloride in ethanol and the crystals are recrystallized from an acetone/ethanol mixture (1:1 v/v/). This gives 15 g (yield: 25%) of CRL 41 000. Melting point=196° C. (with decomposition).

Analysis { % Cl⁻ measured: 14.02%
% Cl⁻ theoretical: 13.79%

The results of the tests which were undertaken with the product of Example 1 (CRL 41 000), which is the preferred compound according to the invention, have been summarized below. In these tests, unless stated otherwise, the CRL 41 000 was administered intraperitoneally in solution in distilled water (pH 5), in a volume of 20 ml/kg to male mice and in a volume of 5 ml/kg to male rats.

TOXICITY

The LD-0 (maximum non-lethal dose) in mice is greater than 256 mg/kg and less than 512 mg/kg.

B. NEUROPSYCHOPHARMACOLOGICAL STUDY

I—Overall Behaviour and Reactivities

Groups of 3 animals are observed before and then 15 minutes, 30 minutes, 1 hour, 2 hours, 3 hours and 24 hours after the administration of CRL 41 000.

(1°) In mice, the observations made at the following doses are:

128 mg/kg: excitation with the presence of stereotype movements and hyperreactivity for 3 hours, and moderate mydriasis for 2 hours;

32 mg/kg: transistory excitation (30 minutes).

(2°) In rats, the observations made at the following doses are:

64 mg/kg: excitation with an increase in the fear reaction and in the reactivity to touch for 3 hours, the presence of stereotype movements (3 hours), piloerection for 2 hours, and mydriasis for 3 hours;

16 mg/kg: stereotypes 2 hours after administration, and mydriasis for 2 to 3 hours;

4 mg/kg: mydriasis for 1 to 3 hours,

II—Investigation of Stereotype Movements

Following the observation of stereotype movements among the symptoms noted, any possible stereotypies which might be induced by CRL 41 000 were investigated. Groups of 6 rats receive CRL 41 000 or amphetamine immediately before being placed in small enclosures, where their stereotype behavior is noted every 10 minutes until the effect wears off.

It is found that CRL 41 000 induces the appearance of stereotype movements in rats. The intensity observed after 16 mg/kg of CRL 41 000 is comparable to that obtained after 2 mg/kg of amphetamine.

III—Interaction With Apomorphine (1°) In mice

Groups of 6 mice receive CRL 41 000 half an hour before the subcutaneous injection of 1 or 16 mg/kg of apomorphine. It is observed that, at doses of 8 and especially of 32 and 128 mg/kg, CRL 41 000 opposes the hypothermic action of apomorphine without modifying the righting behavior and the stereotypies.

(2°) In rats

CRL 41 000 is administered to groups of 6 rats half an hour before the subcutaneous injection of 0.5 mg/kg of apomorphine. It is found that, at a strong dose (64 mg/kg), CRL 41 000 causes potentiation of the stereotypies induced by apomorphine.

IV—Interaction With Amphetamine

Amphetamine (2 mg/kg) is injected intraperitoneally to groups of 6 rats half an hour after the administration of CRL 41 000. It is noted that, at doses of 16 and 64 mg/kg, CRL 41 000 distinctly potentiates the stereotypies induced by amphetamine.

V—Interaction With Reserpine

Four hours after the intraperitoneal injection of 2.5 mg/kg of reserpine, groups of 6 mice receive CRL 41 000. The action of the product to be tested is observed with regard to the hypothermia and ptosis induced by reserpine. It is found that, at doses of 8 mg/kg, 32 mg/kg and 128 mg/kg, CRL 41 000 opposes the hypothermia induced by reserpine. The intensity of the ptosis induced by reserpine is reduced at doses of 32 mg/kg and 128 mg/kg of CRL 41 000.

VI—Interaction With Oxotremorine

CRL 41 000 is administered to groups of 6 mice half an hour before the intraperitoneal injection of 0.5 mg/kg of oxotremorine.

(1°) Action on the temperature

At doses of 2 mg/kg and 8 mg/kg, but especially of 32 mg/kg and 128 mg/kg, CRL 41 000 opposes the hypothermic action of oxotremorine.

(2°) Action on the trembling

At doses of 32 mg/kg and 128 mg/kg, CRL 41 000 reduces the intensity of the trembling due to oxotremorine.

(3°) Action on the peripheral cholinergic symptoms

CRL 41 000 does not substantially modify the signs of peripheral cholinergic stimulation caused by oxotremorine.

VII—Action of the Four Plate Test, Traction and Electric Shock

The test is performed on groups of 10 mice half an hour after the administration of CRL 41 000. It is observed that, at doses of 8 mg/kg, 32 mg/kg and 128 mg/kg, CRL 41 000 causes an increase in the number of punished passes, that it does not cause major motor incapacity and that, at a strong dose (128 mg/kg), it opposes the convulsant effects of electric shock.

VIII—Action on the Spontaneous Motility

Half an hour after they have received CRL 41 000, the mice are placed in an actimeter, where their motility is recorded for 30 minutes. It is found that, at the strongest doses used (64 mg/kg and 128 mg/kg), CRL 41 000 causes a very distinct increase in the spontaneous motor activity of the mice.

IX—Action on the Intergroup Aggressiveness

After they have stayed for 3 weeks in the two halves of a cage divided by an opaque partition, groups of 3 mice receive CRL 41 000. Half an hour later, the two groups from the same cage are brought together by removal of the partition, and the number of fights which occur in 10 minutes is noted. It is found that, at a strong dose (128 mg/kg), CRL 41 000 causes a distinct reduction in the number of fights.

X—Action Towards Some Forms of Behavior Perturbed by Various Agents (1°) Motility reduced by habituation to the enclosure After they have stayed in the actimeters for 18 hours, the mice (6 per dose, 12 control animals) receive CRL 41 000. They are immediately returned to their respective enclosures and, half an hour later, their motility is recorded for 30 minutes.

It is found that, at doses of 32 mg/kg and especially 128 mg/kg, CRL 41 000 causes a resumption in the motor activity of mice accustomed to their enclosure.

(2°) Motility reduced by hypoxic aggression

Half an hour after they have received CRL 41 000, the mice (10 per dose, 20 control animals) are subjected to acute hypobaric anoxia [pressure reduction of 600 mm Hg (i.e. about $8 \times 10^4$ pascals) in 90 seconds; release of vacuum in 45 seconds] and are then placed in an actimeter, where their motility is recorded for 10 minutes.

It is observed that, at a strong dose (128 mg/kg), CRL 41 000 causes a very substantial improvement in the motor recovery in mice whose motility has been depressed following a brief period in a reduced-pressure enclosure.

(3°) Asphyxiant anoxia

Groups of 10 mice receive CRL 41 000 half an hour before the intraperitoneal administration of 32 mg/kg of gallamine triiodoethylate (reference curarizing agent).

It is found that CRL 41 000 does not change the time taken for convulsions and death to occur following asphyxiant anoxia caused by a curarizing agent.

XI—Interaction with Barbital

Half an hour after the administration of CRL 41 000, groups of 10 mice receive an intraperitoneal injection of barbital (220 mg/kg).

As from a dose of 2 mg/kg, CRL 41 000 reduces the duration of the sleep induced by barbital. The maximum effect is obtained at doses of 32 to 128 mg/kg.

XII—Action on the "Behavioral Despair"

Half an hour after they have received CRL 41 000, groups of 6 mice are placed in a beaker filled with water to a height of 6 cm. The total period of immobility between the 2nd and 6th minutes following immersion is noted. It is observed that, at doses of 32 mg/kg and 128 mg/kg, CRL 41 000 causes a distinct reduction in the period of immobility or so-called period of "despair".

XIII—Investigation of a Particular Toxicity in Grouped Mice

Immediately after the administration of CRL 41 000, groups of 10 mice are placed in Plexiglass cages ($20 \times 10 \times 10$ cm). The number of dead animals is noted every hour for 4 hours and after 24 hours. The toxicity of CRL 41 000 is determined under the same conditions on groups of 10 mice placed in cages with one mouse per cage.

Under these conditions, no particular toxicity is observed in the grouped mice, the ratio R=LD-50 for isolated mice/LD-50 for grouped mice being less than or equal to 2. By way of comparison, under the same conditions, the ratio R is 8 for amphetamine and diethylpropion, 6 for methylphenidate, 4 for benzphetamine and 3 for nimifensine.

XIV—Antidepressant Activity on Oral Administration

Two prediction tests (interaction with apomorphine and interaction with reserpine) were used to study the antidepressant effects of CRL 41 000 administered orally to male mice (the CRL 41 000, in these two tests, being administered in solution in distilled water by means of a stomach tube, in a volume of 20 ml/kg).

In these tests, CRL 41 000 proved very active as an antidepressant.

In the clinical trials undertaken on man, the antidepressant activity of CRL 41 000 was also obtained by oral administration.

C. CARDIOVASCULAR STUDY

XV—Action in Pithed Rats

CRL 41 000, administered intravenously in aqueous solution in distilled water, was compared with amphetamine and tyramine by three different techniques on pithed rats. The results obtained [variation in the systolic arterial pressure $\Delta AP$ in mm Hg (1 mm Hg corresponds approximately to $1.333 \times 10^2$ pascals)] have been collated in Tables II, III and IV below.

The results in Tables II, III and IV show that (a) the hypertensive activity of tyramine is totally blocked after pretreatment with reserpine, whereas it is not modified by pretreatment with α-methyltyrosine;

(b) the hypertensive activity of amphetamine is not totally blocked by tyramine (catecholamine depletion), by α-methyltyrosine (blocking of the catecholamine synthesis) or by the association of these two reagents:

(c) on the other hand, the hypertensive activity (2nd phase progressive and lasting 1 hour or more) of CRL 41 000 is totally blocked by tyramine, α-methyltyrosine and the association of the two reagents.

In addition to these stimulant effects, CRL 41 000 has antidepressant effects (antagonism of the hypothermia induced by apomorphine, reserpine and oxotremorine, and reduction in the period of immobility or so-called period of "despair").

These stimulant and antidepressant properties suggest that CRL 41 000 acts in the same way as the amphetamines with, in particular, two differences of effect (group toxicity and hypertensive activity).

In clinical trials, it was observed that, as an antide-

TABLE II

VARIATION IN THE SYSTOLIC ARTERIAL PRESSURE (ΔAP) IN PITHED RATS*
After catecholamine depletion by pretreatment with reserpine (7.5 mg/kg administered intraperitoneally 20 hours before administration by the products to be tested)

| | Tyramine 200 μg/kg administered intravenously | Amphetamine 250 μg/kg administered intravenously | CRL 41 000 30 mg/kg administered intravenously | |
|---|---|---|---|---|
| | | | 1st phase | 2nd phase |
| ΔAP (mm Hg) | 0 | +49 | +30 | 0 |

TABLE III

After blocking of the catecholamine synthesis by pretreatment with α-methyltyrosine (250 mg/kg administered intraperitoneally 20 hours before administration of the products to be tested, and then 250 mg/kg administered intraperitoneally 2 hours before administration)

| | Tyramine 200 μg/kg administered intravenously | Amphetamine 250 μg/kg administered intravenously | CRL 41 000 30 mg/kg administered intravenously | |
|---|---|---|---|---|
| | | | 1st phase | 2nd phase |
| ΔAP (mm Hg) | +19 | +17 | +24 | 0 |

TABLE IV

After blocking of the synthesis with α-methyltyrosine and depletion with reserpine administered, under the conditions given above, before the products to be tested

| | Tyramine 200 μg/kg administered intravenously | Amphetamine 250 μg/kg administered intravenously | CRL 41 000 30 mg/kg administered intravenously | |
|---|---|---|---|---|
| | | | 1st phase | 2nd phase |
| ΔAP (mm Hg) | 0 | +20 | +60 | 0 |

Note
*on groups of 3 animals per product to be tested.

D. TERATOGENIC STUDY

The tests undertaken on rabbits (group of 10 female animals per dose; 15 control animals) according to a protocol comprising
administration of CRL 41 000 by gastrogavage at daily doses of 0, 50, 150 and 200 mg/kg from day 5 to day 18 of gestation, followed by
a cesarean carried out on day 29 of gestation,
demonstrated that, in contrast to certain 2-phenylmorpholine derivatives known in the prior art, CRL 41 000 is devoid of a teratogenic effect.

CONCLUSIONS

The results given above show that CRL 41 000 has the profile of a stimulant for the CNS (excitation in mice and rats, hyperreactivity, increase in the number of punished passes in the four plate test, resumption in the motor activity of mice accustomed to their enclosure, presence of stereotype movements—especially potentiation of the stereotypies induced by apomorphine and amphetamine—and antagonism of the sleep induced by barbital).

pressant, CRL 41 000 gave good results in man when it was administered orally in the form of tablets or gelatine capsules (each containing 10 mg of the said CRL 41 000) at a rate of 2 to 3 tablets or gelatine capsules per day, in the treatment of depressive states.

What is claimed is:

1. A 2-hydroxy-2-phenylmorpholine derivative selected from the group consisting of:
   (i) 4-ethyl-2-hydroxy-3-methyl-2-phenylmorpholine; and
   (ii) non-toxic addition salts thereof.

2. A therapeutic composition which contains, in association with a physiologically acceptable excipient, a pharmaceutically effective amount of 4-ethyl-2-hydroxy-3-methyl-2-phenylmorpholine or one of its non-toxic addition salts, as claimed in claim 1.

3. A method of treatment of depression which comprises administering a pharmaceutically effective amount of a compound according to claim 1.

4. A method of treatment of depression which comprises administering a pharmaceutically effective amount of a composition according to claim 2.

* * * * *